United States Patent
Jang

[11] Patent Number: 5,869,007
[45] Date of Patent: Feb. 9, 1999

[54] CONDUCTING POLYMER BASED ACID/BASE SENSORS

[75] Inventor: Guang-Way Jang, Pasadena, Calif.

[73] Assignee: Gumbs Associates, Inc., East Brunswick, N.J.

[21] Appl. No.: 704,375

[22] Filed: Aug. 22, 1996

[51] Int. Cl.⁶ .................................................. G01N 27/04
[52] U.S. Cl. ..................... 422/82.02; 422/68.1; 422/83; 422/86; 422/90; 422/98; 436/100; 436/101; 436/106; 436/124; 436/149; 436/150; 436/153
[58] Field of Search ................................ 422/68.1, 82.02, 422/83, 86, 90, 98; 436/100, 101, 106, 149, 150, 153, 124

[56] References Cited

U.S. PATENT DOCUMENTS

| | | | |
|---|---|---|---|
| 4,721,601 | 1/1988 | Wrighton et al. | 422/68 |
| 4,820,595 | 4/1989 | MacDianrmid et al. | 429/27 |
| 5,145,645 | 9/1992 | Zakin et al. | 422/98 |
| 5,208,301 | 5/1993 | Epstein et al. | 525/540 |
| 5,250,163 | 10/1993 | Epstein et al. | 204/153.21 |
| 5,252,292 | 10/1993 | Hirata et al. | 422/98 |
| 5,331,287 | 7/1994 | Yamagishi et al. | 324/724 |
| 5,417,150 | 5/1995 | Miller et al. | 73/31.02 |
| 5,536,473 | 7/1996 | Monkman et al. | 422/90 |
| 5,556,700 | 9/1996 | Kaneto et al. | 428/332 |
| 5,585,038 | 12/1996 | Kirmanen et al. | 252/500 |
| 5,624,605 | 4/1997 | Cao et al. | 252/500 |
| 5,756,879 | 5/1998 | Yamagishi et al. | 73/28.01 |

*Primary Examiner*—Jill Warden
*Assistant Examiner*—S. Carrillo
*Attorney, Agent, or Firm*—Omri M. Behr, Esq.

[57] ABSTRACT

Acid/base measuring sensor systems consisting of arrays of basic sensor cells are described which are constructed based on the chemical/electrical response characteristics of poly (aromatic amines). Protonation (doping) or deprotonation (de-doping) of the —N=sites in the polymers leads to characteristic conductivity vs. concentration curves which can be calibrated to produce reliable, instantaneous readings of the acid/base concentrations at various points in the working environment.

17 Claims, 5 Drawing Sheets

CONDUCTING POLYMER BASED ACID/BASE SENSORS

BACKGROUND OF THE INVENTION

Polyaniline is an electroactive and electrically conducting polymer, one member of a class of organic polymers that can be used in chemical sensing. The use of conducting polymers such as polyaniline, polypyrrole and poly(3-hexylthiophene) as chemical sensors for vapors such as ammonia [Hirata, M et al., U.S. Pat. No. 5,252,292 and Selampinar, F. et al., Synthetic Metals 1995, 68, 109], methanol [Boyle, A. et al., Synthetic Metals 1989, 28, C769], water, $NO_2$, and hydrazine [Ellis, D. L. et al., P. M. S. E. 1994, 71, 590] is known. There are comprehensive reviews on the use of electroactive polymers in chemical sensors [Bidan, G., Sensors and Actuators B 1992, 6, 45 and Miasik, J. J. et al., "Conducting Polymers", Alcacer, L. ed. D. Reidel Publishing Co. Boston, 1987, pp189–1981]. Wrighton et al., U.S. Pat. No. 4,717,673, teaches thiophene polymer-based devices which may be used as electrical energy storage devices or as sensors of changes in chemical concentration or pH. A species detector utilizing conductive polymers such as polyaniline is described in Zakin et al., U.S. Pat. No. 5,145,645. A method of orienting polyaniline films in order to increase their electrical conductivity is taught by Theophilou et al., U.S. Pat. No. 5,217,650.

There are three categories of sensors based on electroactive polymers: (a) mass, (b) optical, and (c) electrochemical sensors. There are three main transduction electrochemical modes, giving rise to three types of electrochemical sensors: (i) potentiometric, (ii) amperometric, and (iii) conductimetric sensors.

The electrical conductivity of an electroactive polymer depends on the level of doping or oxidation, i.e., concentration of courterion (dopant). Because the difference in electrical conductivity of an undoped and fully doped polymer is in the vicinity of 9 orders of magnitude, the incremental change of conductivity is the basis for operation of conductimetric, chemical sensors, also known as chemiresistors.

There is a need for a sensor capable of measuring the concentration of acid gases (i.e., HX, where X=F, Cl, Br, I, etc.) in ppm's, for example, in areas where they are is discharged into the environment. For example, federal and local environmental laws require measurement of ground level concentrations of HCl emitted from solid rocket plumes. Decomposition of the oxidizers, typically perchlorates, used in the rocket boosters results in the evolution of large quantities of HCl. Adequate plume characterization requires multiple and widely distributed sampling points. The specific need is for an inexpensive, highly accurate, easily maintained, calibrated, portable instrument with a short response time. None of the current HX monitoring techniques, such as selective ion electrode, chemiluminescence, correlation spectrophotometry and coulometric methods, fits these requirements. Detection of acid gases is also important for industries involved in the incineration of halogenated hydrocarbons and manufacturing of processes resulting in hydrogen halide as a by-product. Detection of HF is very important for the semiconductor industries. It is important to use an accurate monitor because inaccurate measurements of HX gases can lead to overexposure of the public and possible litigation.

Typical start-of-the-art detection instruments have poor response times, and do not measure total (gaseous/aqueous) HX. If they do measure total HX, they are heavy, expensive, and hard to maintain, calibrate and use. Typical collection methods, including pre-evacuated grab sample containers, condensation traps, adsorption tubes, and plastic grab bags, suffer from sample loss prior to analysis and are not suitable for real-time monitoring of HX gases [Bailey, R. R. et al., Analytic Chemistry, 1976, 48, 1818].

Reversible ammonia gas sensors can be accomplished by dispersing a polyaniline in a matrix of a conductive high molecular weight polymer (U.S. Pat. No. 5,252,292). Conductive, high molecular weight polymers may contain ionic side chains or an electrolyte. The resistance of composite films made of conductive high molecular weight polymers increases after exposure to ammonia gas in the ppm range. Miasik et al. ("Electronically Conducting Polymer Gas Sensors", Conducting Polymers, Luis Alcacar, ed., 1987, D. Reidel Pub. Co., pp 189–198) demonstrated that the sensors can be fabricated using polypyrrole for the ambient temperature detection of several industrially important gases, such as ammonia and nitrogen dioxide.

SUMMARY OF THE INVENTION

Acid/base measuring sensor systems consisting of arrays of basic sensor cells are described which are constructed based on the chemical/electrical response characteristics of poly(aromatic amines). The concept is based on the very sensitive and highly reversible dependence of electrical conductivity and optical properties of these conducting polymers when exposed to acidic or basic vapors or species. The resulting protonation (doping) or deprotonation (dedoping) of the —N= sites in the polymers leads to characteristic conductivity vs. concentration curves which can be calibrated to produce reliable, instantaneous readings of the acid/base concentrations at various points in the working environment. The sensitivity of the acid/base sensor of the present invention is in the ppb range.

BRIEF DESCRIPTIONS OF DRAWINGS

FIG. 1 illustrates the representative structural forms of protonated and deprotonated polyaniline.

DETAILED DESCRIPTION OF THE INVENTION

This invention relates to an acid gas (HX, where X=F, Cl, Br, I, etc.) or base gas (e.g., $NH_3$, hydrazine, etc.) sensor and particularly to an acid gas sensor comprising a poly (aromatic amine) as the sensing component of the device. Another aspect of this invention relates to a method of fabricating this sensor and using it to sense acidic or basic gases. Yet another aspect of the invention is the use of an array of sensors with each sensor element of the array having a different doping level.

Poly(aromatic amine) herein means polyaniline and its derivatives, such as poly(ethylaniline), poly(butylaniline), poly(o-toluidine), etc., and the electroactive copolymers of polyaniline with these derivatives. The term is also intended to include the various oxidation states of these polymers.

According to one aspect of the present invention there is provided an HX sensor consisting of at least one pair of electrodes and an HX sensing material comprising a poly (aromatic amine) filling the space between the electrodes. Another aspect of the invention is the use of an array of such sensors with each element of the array having a different doping level. This is preferred because the resolution of the sensor array improves with the addition of each sensor to the array. The sensitivity of each sensor is higher if partially doped poly(aromatic amine) is used, compared to the undoped or heavily doped poly(aromatic amine). The sensitivity also depends on the distance between the two electrodes of each sensor and therefore the array can comprise many sensors wherein the distance between its two electrodes varies from 1 $\mu$ to 1 mm, preferably 5–200 $\mu$, and the doping level varies from 0 to 50%.

According to a further aspect of the invention, this invention relates to a composition comprising a matrix of one or more thermoplastic or thermoset polymers having poly (aromatic amine) dispersed therein, said composition being sandwiched between a pair of electrodes. This invention also relates to a process for preparing a composition comprising a matrix of one or more thermoplastic or thermoset polymers having poly(aromatic amine) dispersed therein, and to a process for preparing the device so that the sensor is capable of detecting concentrations of acid or basic species in both the aqueous and vapor phases below one part per million, preferably below one part per billion.

This invention also relates to a process for detecting an acid or base in either the aqueous or gas phase which comprises contacting a sensor as described herein with an acid or base, measuring an electrical resistance change of the sensing material, and determining the concentration of acid or base from said change in the electrical resistance of the sensing material.

This invention also relates to a sensor array for monitoring a wide range of acid/base concentrations comprising a plurality of sensing elements, each said element having a different doping level. The sensor array may comprise one or more sensing elements, each of which may be prepared by a process which comprises doping poly(aromatic amine) in a dopant solution, de-doping conductive poly(aromatic amine) in a basic solution or gas, or casting poly(aromatic amine) films from a solution of poly(aromatic amine) and dopant. A chemical suitable for doping poly(aromatic amine) is a compound such as HCl, $H_2SO_4$, $H_3PO_4$, HBr or $HClO_4$ or a high molecular weight polymer such as dodecylbenzene or polystyrene which contains an inonic group selected from sulfonic, carboxylic, phosphoric, and selenic acids and salts thereof, such as dioctylsulfosuccinate, sodium salt and poly(vinylsulfonic acid, sodium salt).

A preferred sensor array is one wherein the poly(aromatic amnine) is emeraldine base, wherein said sensing elements comprise poly(armatic amine) films which have been doped at pH 7.0–2.5 or which have a doping percentage of 0–10% (acid sensor), or wherein said sensing elements comprise poly(aromatic amine) films which have been doped at pH 0–2.5 or which have a doping percentage of 5–50% (base sensor).

A preferred sensor array is one wherein a sensing element is prepared by a process which comprises casting poly (aromatic amine) films from a solution of poly(aromatic amine) and dopant on an insulating substrate having at least one pair of electrodes thereon, preferably wherein said films have a doping percentage of 0–10% or a doping percentage of 5–50%. Another preferred sensor array is one wherein the sensing material comprises poly(aromatic amine) dispersed in an inert polymer matrix such as polymethylmethacrylate, polyvinylchloride, or polystyrene.

Figure 1:
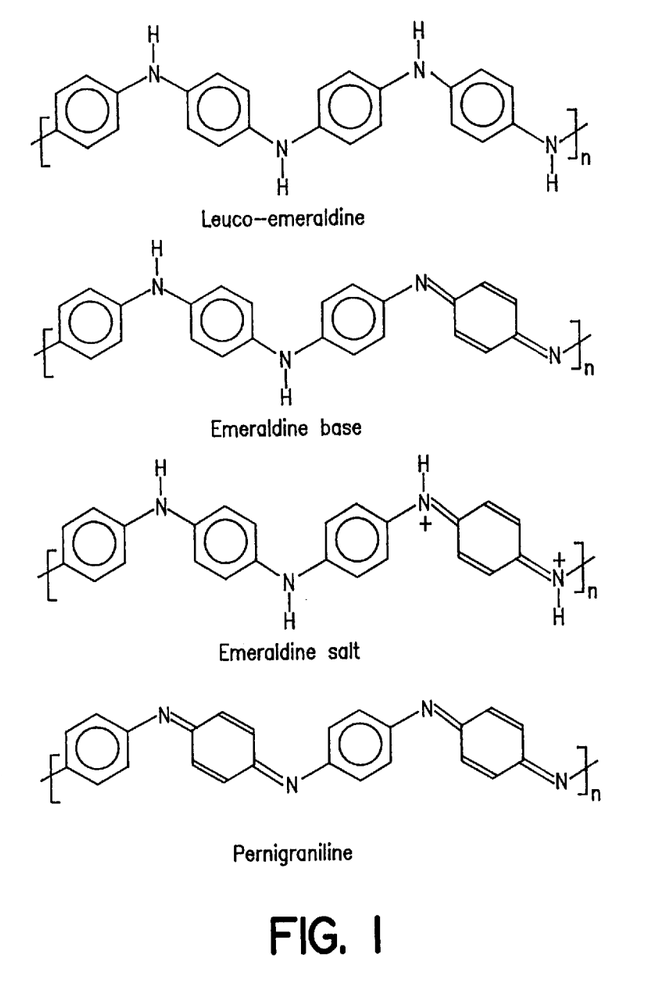
FIG. 1 is a structural representation of polyaniline.

Polyaniline may exist in different stable forms which vary with electrical potential and pH. Under ambient conditions (i.e., 1 atmosphere pressure, at room temperature), the polymer was found (Genies E. M. et al., Synthetic Metals, 1990, 36, 139) to be most stable in its emeraldine oxidation state. The emeraldine base (EB) form of polyaniline consists of equal numbers of the reduced repeat units [—$(C_6H_4)$—N(H)—$(C_6H_4)$—N(H)—] and the deprotonated oxidized repeat units [—$(C_6H_4)$—N=$(C_6H_4)$=N—]. The emeraldine base form of polyaniline has a blue color and its conductivity is less than $10^{-8}$ S/cm. The emeraldine base can be doped to the metallic conducting regime by aqueous protonic acid. The resulting emeraldine salt (ES) has a green color and its conductivity is greater than 1 S/cm. The doping percentage or doping level can be calculated based or the following equation:

$$doping=(X/N)100$$

where X/N represents the molar ratio of dopant ion (X) and nitrogen (N). For example, the doping level of ES of FIG. 1 is 50%. One attractive feature of these materials is their versatility.

Polyaniline is also attractive because it is stable in air, its monomer is relatively inexpensive, and because both the salt (U.S. Pat. No. 5,232,631) and base forms are soluble. Thus films can be cast, permitting the fabrication of relatively inexpensive and disposable devices for deployment over large areas and for personal monitoring badges used by workers who are exposed to small concentrations of gas.

The resistivity of a poly(aromatic amine) decreases upon exposure to acids in both the aqueous [Salaneck, W. R. et al., Synthetic Metals 1987, 18, 291] and vapor phases. This invention utilizes this change in resistance of poly(aromatic amine) film to monitor the concentration of acid/base. The acid/base sensor system of this invention comprises arrays of basic sensor cells. The sensing material is a substituted or unsubstituted polyaniline. The basic sensor cells consist of poly(aromatic amine) coatings with doping level varying from 0 to 50% (i.e., dopant anion/aniline=½). A preferred acid sensor is one wherein the poly(aromatic amine) is emeraldine base which has been doped at pH 7.0–2.5, more preferably at pH 4.0–2.5. A sensor suitable for detecting HCl in ppb concentrations is one wherein the poly(aromatic amine) is emeraldine base which has been doped at pH 3.3–2.5. A preferred base sensor is one wherein the poly (aromatic amine) is emeraldine base which has been doped at pH 0–2.5, more preferably at pH 1.7–2.5. Poly(aromatic amine) films with different doping levels can be prepared by equilibrating the polymer films with solutions of various pH values or by using different solution mixtures of poly (aromatic amine) and dopant to prepare the polymer films.

In addition to varying the doping levels, the detection range of a sensor array can be controlled by varying electrode spacing and/or film thickness. The sensitivity of the a sensor element decreases as electrode spacing or film thickness increases. Therefore, by controlling these three parameters, a highly sensitive sensor array for detection of a wide range of acidic/basic gases can be fabricated. This sensor array will consist of a series of sensor elements which differ from each other in doping levels, film thicknesses, and electrode spacing.

This invention also utilizes color change to monitor the concentration of acid/base. The emeraldine base form of polyaniline is blue; the acidic form is green. The near IR and the IR absorbance also changes as a function of pH. Polyaniline, therefore, can be deposited on an optical fiber and used as a sensor to monitor gas concentration based on changes in a absorbance in the visible, near IR, and IR spectra.

The poly(aromatic amine) used as the HX sensing component in the HX sensing material of the sensor of the present invention is typically prepared by chemical or electrochemical polymerization of the appropriate aromatic amine (e.g., aniline). The solid material resulting from the oxidation of aniline is the conductive and fully doped form of polyaniline. This is subsequently converted into the base form by treatment with aqueous ammonia, yielding emeraldine base, which is nonconductive. Aniline is chemically polymerized in 1M aqueous HCl in the presence of an oxidant such as ammonium persulfate. If emeraldine base having a conductivity of $10^{-9}$ S/cm is immersed in 1M HCl, it is converted into emeraldine HCl with a conductivity of 1–25 S/cm. Thus, polyaniline is an ideal candidate for sensing HCl.

The electrical conductivity and optical properties of poly (aromatic amine) show a unique dependence on pH and oxidation state. These polymers can be transformed from the insulating state ($<10^{-8}$ S/cm) to the conducting state ($>1$ S/cm) by exposure to an acidic vapor. In addition, the color of these polymers changes from blue to green upon protonation (doping). The dependence of the conductivity and color of these polymers on the pH of the environment indicates that these polymers are ideal candidates for the fabrication of HX sensors.

The conductivity of poly(aromatic amine) can be controlled by acid/base treatment and/or electrochemical reduction and oxidation. In general, the conductivity of poly (aromatic amine) increases as the pH of solution decreases. The conductivity of polyaniline in the emeraldine oxidation state is most sensitive to pH change between pH=4 and pH=1. At pH >4 and <1, the conductivity of polyaniline is almost independent of pH change. This indicates that the response time and sensitivity of an acid sensor can be improved by using lightly doped (protonated) polyaniline. On the other hand, the performance of the sensor for monitoring basic species, such as ammonia, can be improved by using polymer doped with pH~1 solution. Monitoring a wide range HX concentration can be accomplished by using a sensor array consisting of poly(aromatic amine) films with various doping levels. The resolution of the sensor arrays can be increased by increasing the number of sensor cells.

Polymer films, in the emeraldine oxidation state, can be equilibrated with solutions of various pH values to vary their doping level. Alternatively, polymeric dopant can be incorporated into poly(aromatic amines) at various percentage during polymerization or post-polymerization in order to control the doping level of the polymers. Postpolymerization treatments include but are not limited to electrochemical or chemical doping and mixing of solutions or solids of emeraldine base forms of poly(aromatic amines) and doping materials.

When the sensor array is exposed to a low concentration of acids (HCl, HF, HBr, etc.), the resistance change of the lightly doped poly(aromatic amines) is much higher than the heavily doped and emeraldine base forms of the polymers. On the other hand, the resistance of all sensor cells will decrease rapidly when exposed to a high concentration of acids. The acid concentration can be estimated by (1) the number of sensor cells whose conductivity reach a preset value, and/or (2) the resistance change of each sensor cell, and/or (3) the rate or resistance change of each sensor cell. For example, each sensor cell can be designed to be used as on/off switch of a light bulb. The switch will turn on when the resistance of the polymer film decreases to a certain value or change at a certain rate. The concentration of acid, therefore, can be measured based on the number of lights that are on. The electrodes for resistance measurements can be interdigitated electrodes (such as AAI Model 1550 series, Abtech, Yardley, Pa.) or any other types; for example, a rectangular poly(aromatic amine) film sandwiched between electrodes.

Poly(aromatic amines) are effective HX and ammonia sensing materials and the measurement of the resistance changes enables the detection of their concentration with very high sensitivity. The sensitivity of the poly(aromatic amine) based sensor can be further enhanced by using a partially doped poly(aromatic amine). An array of basic sensor cells consists of poly(aromatic amine) with various doping levels which can be used for monitoring a wide range of acid/base concentrations. The sensor fabricated on the interdigitated electrode can be interfaced with a portable computer via a multimeter used to measure resistance. Thus, data acquisition can be automated. This means that real time data logging is possible with the device.

The essential ingredient in the electroactive matrix is polyaniline (FIG. 1), its derivatives, and its copolymers of these derivatives. In general, polyaniline for use in this invention is a homopolymer derived from polymerization of aniline. Substituted anilines can be conveniently used in the practice of this invention. Useful polyanilines can be prepared through use of chemical and electrochemical synthetic procedures. One form can be prepared by treating aniline with ammonium persulfate in excess aqueous 1M hydrochloric acid at 0°–5° C. This powdered form is blue-green in color. After washing with 1M HCl and air drying, this material, emeraldine hydrochloride, has a conductivity of 1–10 S/cm, depending on its moisture content. This conductive form of polyaniline and indeed all conductive forms, can be treated with 0.1M ammonium hydroxide in water to form a non-conductive form of polyaniline, emeraldine base. Numerous other chemical procedures for preparing various chemical forms of polyaniline have been reviewed in detail, (Genies et al., Synthetic Metals, 1990, 36, 139).

The base form of polyaniline is soluble in some organic solvents such as N-methylpyrrolidone, tetrahydrofuran, and N,N'-dimethylformamide. For application in an acid/base sensor, the polyaniline can be dissolved in an organic solvent or a mixture of such organic solvents. The resulting solution can be coated on an insulating substrate having at least one pair of electrodes thereon, so as to fill the space between the electrodes.

Useful forms of poly(aromatic amine) can also be prepared electrochemically. For example, polyaniline can be prepared by electrochemical oxidation of aniline in aqueous acids on a platinum foil electrode. Electrochemical procedures for preparing polyaniline have also been reviewed in Genies et al., Synthetic Metals, 1990, 36, 139. One advantage of the electrochemical method is that thin films can be deposited on one of the electrodes of the device and that their thickness can be controlled. Another advantage is increased speed of fabricating the device. The resulting polymers can be dissolved in an organic solvent and coated on the substrates consisting of at least two electrodes. The polyaniline can also be electrochemically deposited on and between the electrodes on insulating substrates.

Poly(aromatic amine) can be electrochemically or chemically oxidized (doped) or reduced (de-doped) to various oxidation states. For example, as synthesized, polyaniline is about 50% doped, i.e., has an equal amount of reduced and oxidized units. Polyaniline has its highest conductivity at this oxidation state. As synthesized, polyaniline can be reduced by using reducing agents such as hydrazine or ascorbic acid or it can be oxidized by oxidants such as $(NH_4)S_2O_3$, $FeCl_3$, or $Cu(BF_4)_2$. However, oxidation and reduction of poly(aromatic amine) can be carried out more controllably by means of electrochemical techniques, such as in an electrochemical cell containing suitable electrolyte solutions. Two-electrode (working and counter) and three-electrode (reference, working, and counter) configurations have been used for this application. Poly(aromatic amine) can be electrochemically deposited on conductive substrates such as platinum, gold, ITO (indium-doped tin oxide), and graphite. Chemically synthesized poly(aromatic amine) in solution can be brush, spin, or spray coated on these substrates. A conductive substrate coated with poly(aromatic amine) is used as the working electrode. A standard calomel electrode (SCE) and Ag/AgCl are the most frequently used reference electrodes. The counter electrode is usually platinum, graphite, or gold foil or mesh. A typical electrolyte solution for doping poly(aromatic amine) is 1M HCl or $H_2SO_4$. Other electrolytes, such as $LiClO_4$, $HClO_4$, HBr, $HBF_4$, tetraethylammonium tetrafluoroborate, tetraethylammonium p-toluene sulfonate, tetraethylammonium bromide, camphoric acid, poly(vinylsulfonic acid), poly(styrene sulfonic acid), and solvents such as acetonitrile, propylene carbonate, benzonitrile, THF, and DMF, have also been used to prepare electrolyte solutions for electrochemical oxidation and reduction of poly(aromatic amine). The potential of the working electrode vs. the reference electrode can be controlled (i.e., varied) with a potentiostat. The potential of the working electrode can be stepped or scanned at a constant speed to a preset value and then held for a few seconds or minutes, depending on the poly(aromatic amine) film thickness. The resistance of polyaniline film is most sensitive to its oxidation state at a potential range between 0 and +0.2 and between +0.6 and +0.8 V. Polyaniline has its highest conductivity or lowest resistance at about +0.4 V vs. SCE. At this potential, polyaniline is 50% doped.

Other chemical and electrochemical synthetic methods and transformations of poly(aromatic amine) are within the scope of the invention. Moreover, additional forms or types of poly(aromatic amine) may be elucidated and are within the scope of the invention. In addition to the use of derivatives of aniline as monomer, mixtures of monomer can be used to prepare electroactive copolymers. These are also useful in the invention. Accordingly, no limitation to the syntheses, transformation, or structures herein described is intended.

Another aspect of this invention relates to a composition comprising one or more solution processible thermoplastic or thermoset polymers. One advantage of this composition is that the properties of the insulating matrix may be incorporated into the electroactive film. The proportion of poly(aromatic amine) to thermoplastic or thermoset polymer is not critical and may vary widely, depending on the environment in which the sensors will be deployed.

The composition of this matrix can be prepared using conventional solution blending techniques such as ball milling or ultrasonic mixing. The composition may be applied to the electrode by conventional methods such as spray, brush, roller, blade, etc. In the preferred embodiments of the invention the poly(aromatic amine) is mixed with the solvent by ultrasonication. Thereafter the thermoplastic or thermoset polymer is added to the solution. The order of mixing is not critical. Accordingly, the order of addition of the polymer and any other additives to form the intimate mixture used for coating the electrode and described in the examples given below can be varied as desired.

The following specific examples are presented to more particularly illustrate the invention, and should not be construed as being limitations on the scope and spirit of the invention.

EXAMPLE 1

Polyaniline was synthesized according to the chemical method described by MacDiarmid, A. G. et al. (Conducting Polymers, Alcacer, L. ed. 1987, pp105–120). The resulting conductive polyaniline (emeraldine hydrochloride) was suspended in 0.1M $NH_4OH$ to produce emeraldine base.

Figure 2:
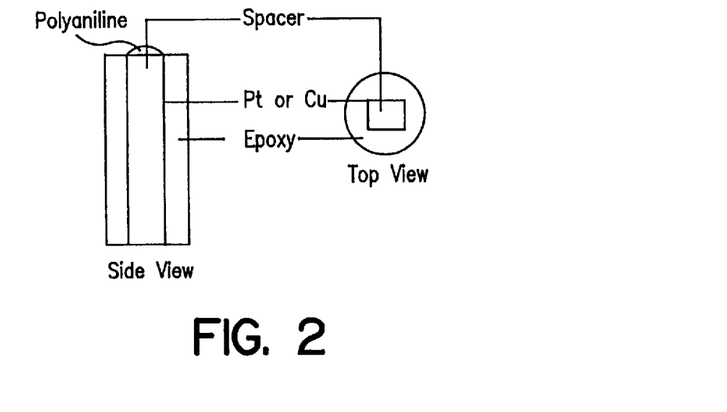
FIG. 2 is a representative sensor cell.

The sensor cell, such as depicted in FIG. 2, for resistant measurement was prepared according to the following method. A strip of rectangular polyester film (4×40×0.14 mm) was sandwiched between two copper electrodes (4×15 mm). The polyester film and copper electrodes were then glued together using an epoxy adhesive. The electrodes were covered with Teflon tape, except for one edge (4 mm wide). A solution of the emeraldine base (1%) in N-methylpyrrolidone was coated on the exposed edges of the two electrodes and polyester film. The resulting polyaniline coating was then doped with HCl aqueous solutions at various pHs.

Figure 3:
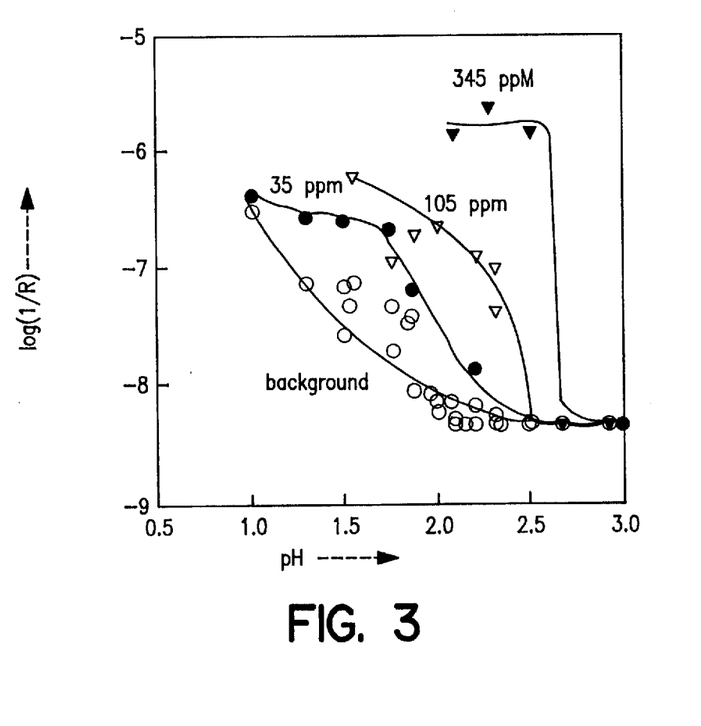
FIG. 3 is a plot of delta log(1/R) versus pH, showing sensor array test results for the polyaniline sensor prepared according to Example 1.

For evaluation of the sensor, three HCl solutions of different concentrations in ethyl ether were introduced into 4.4 L filtering flasks using disposable serological pipettes. The HCl solutions were stirred with triangular plastic flags and allowed to evaporate at room temperature. The maximum concentration of HCl gas generated from the 1 mL of 10 mM HCl-ether solution in a 4.4 L glass flask was calculated to be 350 ppm (1 ppm =240 $\mu g/m^3$), assuming 100% evaporation of HCl and no absorption of HCl on the glass wall and other objects. Based on this assumption, 1 mL of 3 mM HCl-ether solution and 1 mL 1 mM HCl-ether solution are calculated to produce 105 ppm and 35 ppm HCl gas, respectively, under the same conditions. After about one minute of mixing, the sensor was exposed to the gas mixtures and the resistivity of the polyaniline coating as a function of exposure time was recorded. The resistance of polyaniline coatings reached a steady reading in about 3 minutes. FIG. 3 shows the conductivity changes (delta log(1/R)) of sensor cells consisting of polyaniline film at various doping levels when exposed to HCl gas at three concentration levels. The doping level of polyaniline increases as the pH value of the doping solution decreases.

EXAMPLE 2

An HCl sensor was fabricated using poly(o-toluidine) as the sensing material. In this configuration, a sandwich structure of platinum foil/polyester film/platinum foil/polyester film/platinum foil was prepared according to the procedure described in Example 1. The structure here was embedded in epoxy instead of Teflon tape. After hardening of the embedding material, it was polished with sandpaper to expose 3 mm long edges of the three platinum foils.

Figure 4:
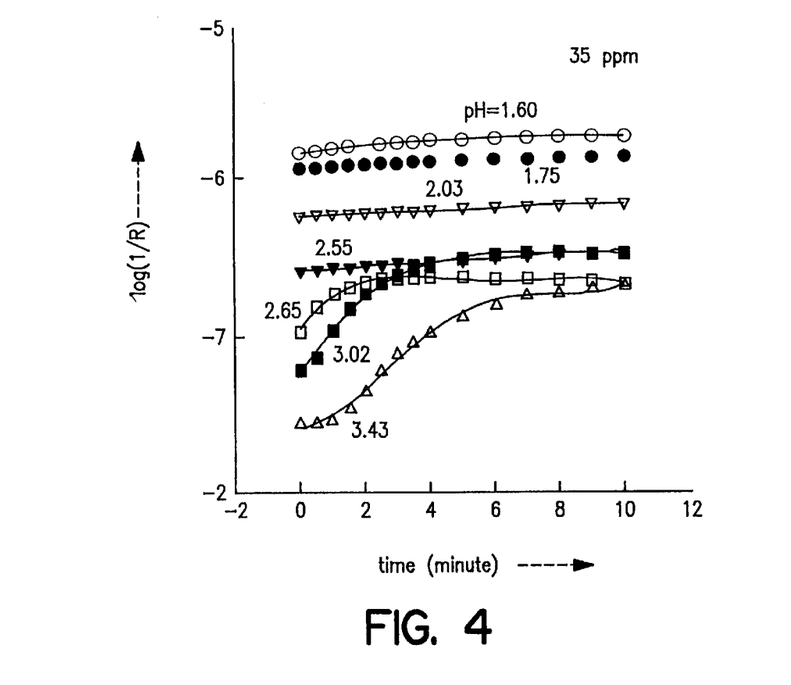
FIG. 4 is a plot of log (1/R) vs time, showing the response of poly(o-toluidine) film in an atmosphere of 35 ppm HCl at room temperature.

Emeraldine base of poly(o-toluidine) was prepared according to the same procedure for preparing emeraldine base of polyaniline. The resulting blue color emeraldine base form of poly(o-toluidine) was dissolved in N-methylpyrrolidone to form a 1% polymer solution. This solution was coated on the exposed area of the platinum electrodes and polyester spacers. The conductivity of poly (o-toluidine) coatings between the center electrode and the two electrodes on the outside was measured using a Keithley 617 electrometer. FIG. 4 shows the responses (log(1/R)) of the poly(o-toluidine) coating at various doping levels as a function of time. The HCl gas was produced by introducing 1 mL 1 mM HCl-ether solution in a 4.4 L glass flask. The maximum concentration of HCl vapor was calculated to be 35 ppm.

EXAMPLE 3

An HCl sensor consisting of two platinum foils as electrodes, a polyester film as spacer and poly(ethylaniline) as sensing material was fabricated according to the method described in Example 2. The length of platinum electrode exposed was 4 mm. For the poly(ethylaniline) film predoped in a pH=3.03 HCl solution, the resistance of the polymer film decreased from $3.81 \times 10^{10}$ Ω to $3.25 \times 10^{10}$ Ω when exposed to a HCl gas produced by evaporating 1 mL 3 mM of HCl-ether solution in a 4.4 L glass flask. The resistance change of poly(ethylaniline) film was lower than that of polyaniline or poly(o-toluidine) when exposed to the same concentration of HCl gas.

EXAMPLE 4

Polyaniline film was electrochemically deposited on an Abtech IME 1550-M interdigitated electrode by cycling the potential of the electrode between −0.2 V and +0.8 V vs. SCE for 13 cycles in a 1M HCl solution containing 0.2M aniline. Pyrolytic graphite was used as a counter-electrode for the synthesis of polyaniline. The basic pattern of the interdigitated electrodes consisted of two platinum electrodes deposited on a borosilicate glass plate. Each electrode has 50 sets of interlaced lines. The line length, width, and spacing are 0.5 cm, 15 μm, and 15 μm, respectively. The polymer was allowed to grow across the fine interelectrode gap. The resulting polyaniline film was then de-doped in a 0.1M $NH_4OH$ solution to produce emeraldine base and dried in an oven at 75° C.

Figure 5:
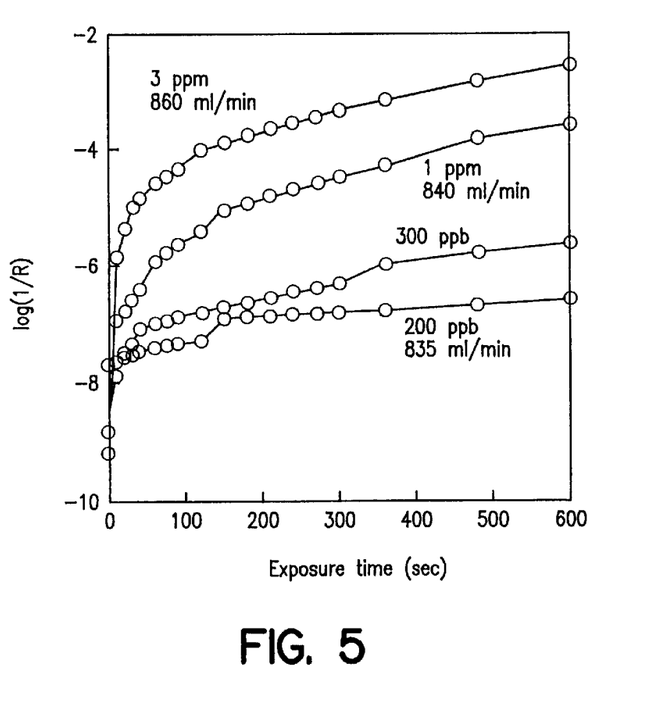
FIG. 5 shows the response of an electrochemically deposited polyaniline film on an interdigitated electrode.

An $HCl/N_2$ gas mixture containing 100 ppm HCl was used as the gas source for sensor testing. The HCl gas source at flow rates of 29.4 mL/min., 8.9 mL/min., 2.6 mL/min., and 1.8 mL/min. was mixed with $N_2$ gas at a flow rate of 833 mL/min. in a two-tube gas proportioner to generate 3 ppm, 1 ppm, 500 ppb and 200 ppb HCl gas sources. The concentration of HCl was expected to decrease gradually in the source. However, its original concentration was used to estimate the HCl concentration after dilution. FIG. 5 shows the response of emeraldine base film when exposed to HCl gas at various concentrations.

EXAMPLE 5

Figure 6:
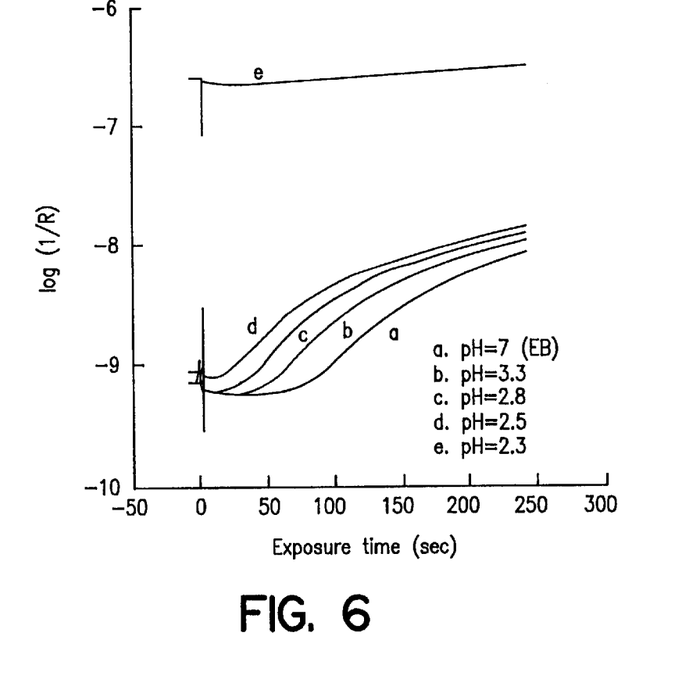
FIG. 6 shows the response of a film cast from a solution of polyaniline, which was prepared chemically, on an interdigitated electrode.

The emeraldine base solution of Example 1 was deposited on an interdigitated electrode. The electrode was similar to the one used in Example 4 expect that the line spacing was 10 μm. The polyaniline films at various doping levels were exposed to 200 ppb HCl gas prepared by the method described in Example 4. As shown in FIG. 5, the lightly doped polyaniline films (pH=3.3, 2.8, and 2.5) were more sensitive to low concentration of HCl vapor than the heavily doped (pH=2.3) and undoped (EB) films. The response time and rate of resistance changes were very sensitive to the pH between 4 and 2.5. A small deviation could result a sharp change in sensor performance. However, the responses of the lightly doped polyaniline films always fell between curves b and d of FIG. 6. This clearly indicates that the sensor sensitivity can be improved by using lightly doped polymer.

EXAMPLE 6

Figure 7:
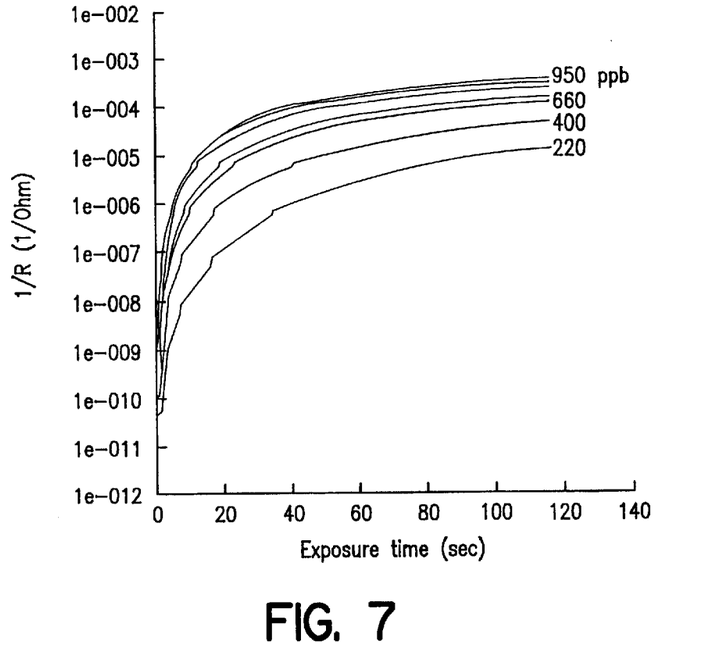
FIG. 7 shows the response of a spin coated polyaniline film on an interdigitated electrode.

Polyaniline thin film can also be obtained by known spin coating techniques. A very uniform coating was obtained by this technique. This also improved the performance of the gas sensor. FIG. 7 shows the response of a spin coated polyaniline film on an interdigitated electrode at various HCl concentrations.

EXAMPLE 7

Figure 8:
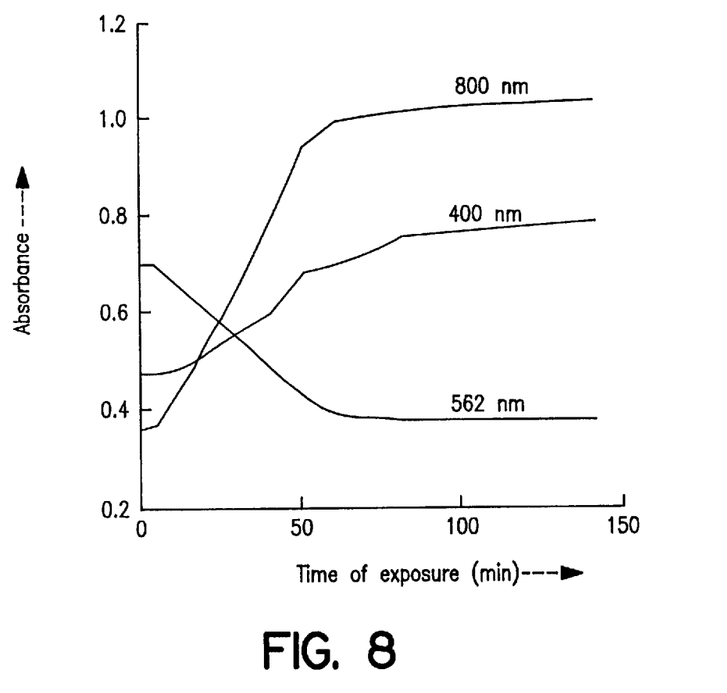
FIG. 8 is a plot of absorbance vs time of exposure of poly(o-toluidine) to HCl.

The effects of HCl vapor on the optical properties of poly(o-toluidine) were investigated. The polymer film was deposited on an indium tin oxide (ITO) glass by in-situ polymerization in a chemical reaction chamber. The polymer film was exposed to HCl vapor which was generated by bubbling nitrogen gas through 0.66M HCl aqueous solution at a flow rate of about 2.2 L/min. FIG. 8 represents the absorbance-time profiles of the polymer film. This indicates that poly(aromatic amines) can be incorporated into optical fiber technology to fabricate an HCl gas sensor.

EXAMPLE 8

Polyaniline film can also be used for monitoring HF and HBr gases. The emeraldine base solution of Example 1 was deposited on an interdigitated electrode. The electrode was the same as the one used in Example 4. When the polyaniline was exposed to HF or HBr gases for about 1 minute, its resistivity decreased about 8–9 orders magnitude.

What is claimed is:

1. An acid sensor consisting of at least one pair of electrodes and an acid sensing material between said electrodes, wherein the acid sensing material comprises a polyaniline which has been doped at a pH of 2.5–7.0 for detection of an acid.

2. The acid sensor of claim 1, wherein said polyaniline is produced by electrochemical polymerization of aniline.

3. The acid sensor of claim 1, wherein said polyaniline is prepared by chemical oxidation of aniline.

4. The acid sensor of claim 1, wherein said polyaniline is in an emeraldine base form which has been doped at a pH of 2.5–4.0.

5. The acid sensor of claim 1, wherein said polyaniline is in an emeraldine base form which has been doped at a pH of 2.5–3.3 for detection of hydrochloric acid.

6. The acid sensor of claim 1, wherein said polyaniline is dispersed in an inert polymer matrix.

7. The acid sensor of claim 1, wherein the polyaniline is an electroactive substituted polyaniline selected from the group consisting of poly(ethylaniline), poly(butylaniline), and poly(o-toluidine).

8. The acid sensor of claim 1, wherein the polyaniline is a copolymer of aniline and substituted aniline, wherein the substituted aniline is selected from the group consisting of poly(ethylaniline), poly(butylaniline), and poly(o-toluidine).

9. A process for determining a concentration of an acid in an aqueous phase or a gas phase which comprises a) contacting the acid sensor of claim 1 with an acid; b) measuring a change in electrical resistance of the polyaniline; and c) determining the concentration of said acid from said change in said electrical resistance.

10. A base sensor consisting of at least one pair of electrodes and a base sensing material between said electrodes, wherein the base sensing material comprises a polyaniline which has been doped at a pH of 0–2.5 for detection of a base.

11. The base sensor of claim 10, wherein said polyaniline is produced by electrochemical polymerization of aniline.

12. The base sensor of claim 10, wherein said polyaniline is prepared by chemical oxidation of aniline.

13. The base sensor of claim 10, wherein said polyaniline is in an emeraldine base form which has been doped at a pH of 1.7–2.5.

14. The base sensor of claim 10, wherein said polyaniline is dispersed in an inert polymer matrix.

15. The base sensor of claim 10, wherein the polyaniline is an electroactive substituted polyaniline selected from the group consisting of poly(ethylaniline), poly(butylaniline), and poly(o-toluidine).

16. The base sensor of claim 10, wherein the polyaniline is a copolymer of aniline and substituted aniline, wherein the substituted aniline is selected from the group consisting of poly(ethylaniline), poly(butylaniline), and poly(o-toluidine).

17. A process for determining a concentration of an acid in an aqueous phase or a gas phase which comprises a) contacting the base sensor of claim 10 with a base; b) measuring a change in electrical resistance of the polyaniline; and c) determining the concentration of said base from said change in said electrical resistance.

* * * * *